(12) United States Patent
Haas

(10) Patent No.: US 6,484,723 B2
(45) Date of Patent: Nov. 26, 2002

(54) TRACHEOSTOMY AIR FILTRATION SYSTEM

(76) Inventor: Eileen Haas, 90 Kaufman Rd., Gibsonia, PA (US) 15044

( * ) Notice: Subject to any disclaimer, the term of this patent is extended or adjusted under 35 U.S.C. 154(b) by 0 days.

(21) Appl. No.: 09/249,682

(22) Filed: Feb. 11, 1999

(65) Prior Publication Data

US 2001/0013348 A1 Aug. 16, 2001

(51) Int. Cl.[7] .......................... A61M 16/00; A62B 9/06
(52) U.S. Cl. ........................ 128/207.14; 128/206.15; 128/207.16
(58) Field of Search .................. 128/200.26, 207.14, 128/207.15, 207.16, 205.27, 205.25, 205.24, 206.21, 206.15, 206.12

(56) References Cited

U.S. PATENT DOCUMENTS

| | | | | |
|---|---|---|---|---|
| 3,262,447 A | * | 7/1966 | Burke | 128/207.14 |
| 3,461,877 A | * | 8/1969 | Morch | 128/207.14 |
| 3,670,726 A | * | 6/1972 | Mahon et al. | 128/204.18 |
| 4,045,058 A | * | 8/1977 | Eross | 285/119 |
| 4,152,017 A | * | 5/1979 | Abramson | 285/260 |
| 4,416,273 A | * | 11/1983 | Grimes | 128/207.16 |
| 4,676,241 A | * | 6/1987 | Webb et al. | 128/207.14 |
| 5,022,394 A | * | 6/1991 | Chmielinski | 128/207.14 |
| 5,054,482 A | * | 10/1991 | Bales | 128/207.14 |
| 5,062,420 A | * | 11/1991 | Levine | 128/204.18 |
| 5,184,611 A | * | 2/1993 | Turnbull | 128/207.14 |
| 5,251,617 A | * | 10/1993 | Linder | 128/200.26 |
| 5,259,376 A | * | 11/1993 | Bales | 128/207.17 |
| D350,394 S | * | 9/1994 | Kazal | D24/164 |
| 5,368,734 A | * | 11/1994 | Wnenchak | 210/505 |
| 5,380,580 A | * | 1/1995 | Rodgers et al. | 428/219 |
| 5,496,507 A | * | 3/1996 | Angadjivand et al. | 264/423 |
| 5,666,950 A | * | 9/1997 | Smith | 128/207.14 |
| 5,694,922 A | * | 12/1997 | Palmer | 128/202.27 |
| 5,749,360 A | * | 5/1998 | Lacey et al. | 128/207.14 |
| 5,771,885 A | * | 6/1998 | Putrello | 128/205.27 |
| 5,840,091 A | * | 11/1998 | Strong | 55/385.1 |
| 5,890,488 A | * | 4/1999 | Burden | 128/200.26 |
| 6,119,691 A | * | 9/2000 | Angadjivand et al. | 128/206.19 |

* cited by examiner

Primary Examiner—Dennis Ruhl
Assistant Examiner—Joseph F. Weiss, Jr.
(74) Attorney, Agent, or Firm—Susan E. Nagel

(57) ABSTRACT

In the present invention, personal air filtration unit sold as SMARTMOUTH™, a trademark for a personal air filtration unit comprised of an outer activated carbon pre-filter and an inner filter for particulate matter available through Tri-Pact Enterprises has been attached to a column of valve connectors which are connected to a tracheostomy tube. The filter has a downwardly dependent exhaust port which allows expired air to flow out of the filtration unit without passing through the filters, thereby helping to prevent mixing of inhaled and exhaled air, and decreasing resistance to exhalation, as well as one-way valves in the form of a flap, on the one hand to prevent exhaled air from entering a dead space between filters, and on the other hand to prevent entering of inhaled air through the exhaust port.

5 Claims, 2 Drawing Sheets

TRACHEOSTOMY AIR FILTRATION SYSTEM

BACKGROUND

1) Field of the Invention

This invention pertains to breathing devices for patients with tracheostomies.

2) Description of the Related Art

Devices exist which may be utilized by patients with tracheostomies to humidify and to filter inhaled air. The prior art seems to be lacking, however, in a filter which may be attached to a tracheostomy tube which provides an outer activated carbon pre-filter and an inner filter for particulate matter with one-way valve in the form of a flap to prevent exhaled air from entering the filters as well as an exhaust port with one-way valve in the form of a flap to allow for outward flow of expelled air, which helps to prevent mixing of inhaled and exhaled air and decrease resistance to exhalation. The terms "outer" and "inner" are in reference to the structure of the filter and the direction of inhaled air; the "outer" filter is located at the outer extent of the filter and is the filter through which inhaled air passes first. The "iner" filter is located proximal to the "outer" filter, and is the second filter through which inhaled air passes. U.S. Pat. No. 5,666,950 to Smith discloses a filter device for a tracheostoma with an activated carbon and hydrophic layer, but which does not include an exhaust port or one-way valves. U.S. Pat. No. 3,262,447 to Burke discloses an inhalation valve and exhalation valve in a respirator for laryngectomies; however the inhalation valve comprises a structure different from and works differently from that of this invention. The inclusion of an exhaust port and the one-way valves makes the invention particularly useful to those patients whose respiratory status is the most delicate, as it helps to maximize the presentation of filtered air to the patient and the ease with which it is presented.

In the present invention, a personal air filtration unit sold as SMARTMOUTH™ available through Tri-Pact Enterprises, which includes an activated carbon pre-filter and filter for particulate matter, as well as an exhaust port, and one-way valves has been attached to a column of valve connectors, firstly to a conical "multiadaptor" provided by Hudson, which is in turn connected to a cylindrical connector which is available through Instrumentation Industries which is in turn connected to a trach swivel adaptor, such as a "double swivel elbow" by Intersurgical Co. and "trach swivel adaptor" by Marquest Medical Co., which is in turn connected to a patient's tracheostomy tube.

SUMMARY OF INVENTION

In the present invention, a personal air filtration unit (5) has been attached to a column of valve connectors, firstly to a conical "multiadaptor" provided by Hudson, which is in turn connected to a cylindrical connector which is available through Instrumentation Industries which is in turn connected to a trach swivel adaptor, such as a "double swivel elbow" by Intersurgical Co. and "trach swivel adaptor" by Marquest Medical Co., which is in turn connected to a patient's tracheostomy tube.

The filtration unit (5) includes an outer activated carbon pre-filter and an inner filter for particulate matter. Proxhnally from the inner filter for particulate matter is a one-way valve in the form of a flap which allows air to be inhaled through the inner filter but prevents exhaled air from entering dead space between the filters. The filtration unit (5) also has a downwardly dependent exhaust port with it's own one-way valve in the form of a flap which allows expired air to flow out of the fixation unit without passing through the filters, thereby helping to preventing of inhaled and exhaled air and decreasing resistance to exhalation. This one-way valve prevents air from being drawn into the port with inhalation.

DESCRIPTION OF PREFERRED EMBODIMENT

Figure 1:
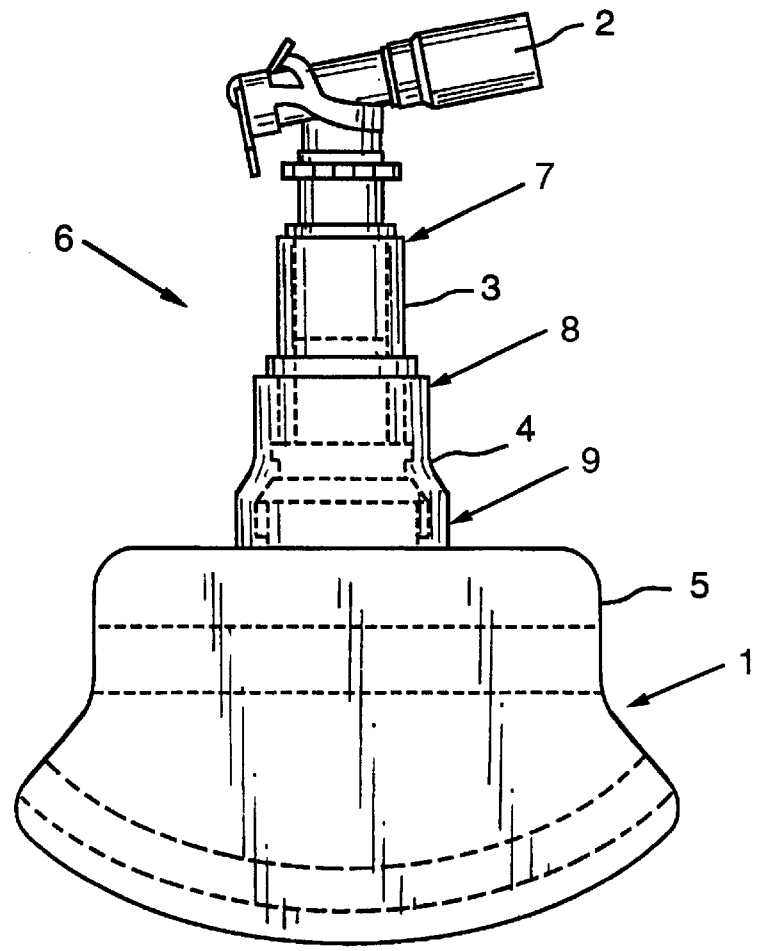
FIG. 1 is a back view of the invention.
Figure 2:
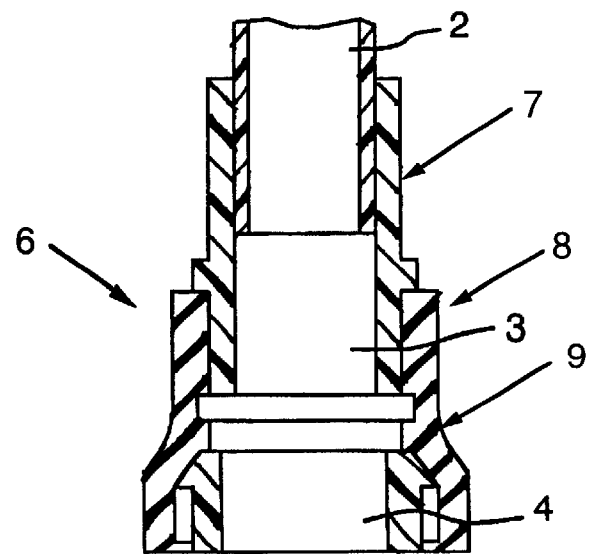
FIG. 2 is a cross-sectional view of the invention.
Figure 3:
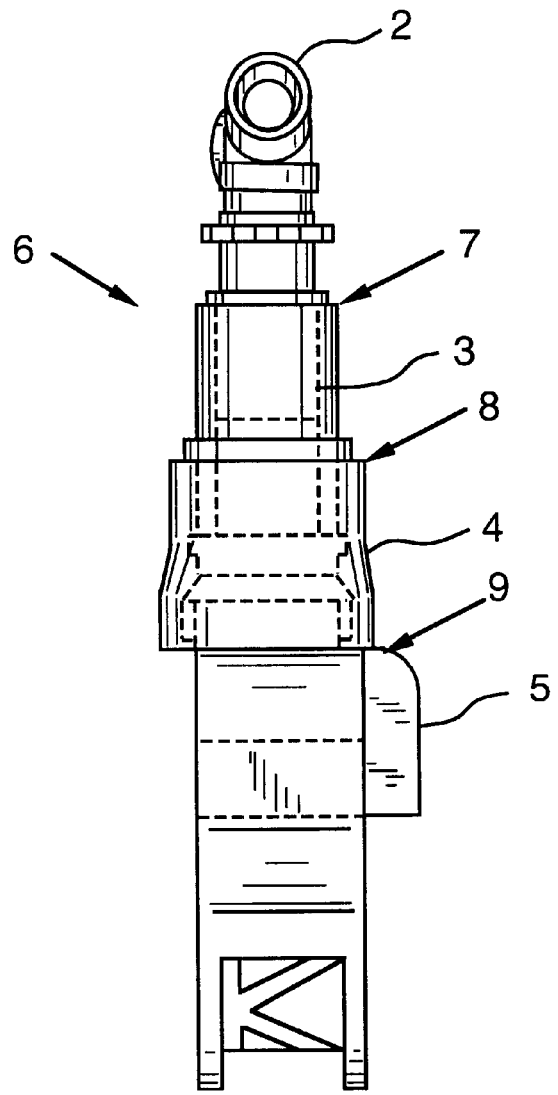
FIG. 3 is a side view of the intention.

The tracheostomy breathing aid (1) as may be reviewed in FIGS. 1 and 3, entails a column (6) of three connectors the latter which is, in turn, connected to the filtration unit (5) The filtration unit (5) includes an outer activated carbon pre-filter (11) and an inner filter for particulate matter (12). Proximally from the inner particulate matter filter (12) is a one-way valve (13) in the form of a flap which allows air to be inhaled through the inner filter (11) but prevents exhaled air from entering the dead space (15) between the filters. The filtration unit (5) also has a downwardly dependent exhaust port (10) with its own one-way valve (14), in the form of a flap, the exhaust port (10) allowing expired air to flow out of the filtration unit (5) without passing through filters (11) and filter (12), thereby helping to prevent mixing of inhaled and exhaled air, and decreasing resistance to exhalation. The valve (14) prevents air from being drawn into the port (10) with inhalation. The trach swivel adaptor (2) is connected at its superior aspect to patient's tracheostomy tube and at its inferior aspect to the superior aspect of cylindrical multiadaptor valve connector (3), forming first connection (7). The cylindrical multiadaptor valve connector (3) is connected at its inferior aspect to the narrow superior aspect of conical valve connector (4), forming second connection (8); the wide inferior aspect of conical valve connector (4) is connected to the filtration unit (5), forming third connection (9). The shape of the conical valve connector (4) is enabling to the invention to allow a connection (9) between the conical valve connector (4) and filtration unit (5), as connector (4) is more narrow than the wider opening of the filtration unit (5). As may be reviewed in FIGS. 2 and 4, the trach swivel adaptor (2) connects to cylindrical multiadaptor connector (3) by way of insertion of the adaptor (2) into the connector (3) which is then tightly secured to adaptor (2) to help form the column (6) The cylindrical multiadaptor connector (3) is connected to the conical valve connector (4) by way of inserting into the connector (4), which also helps to form another component of the column (6). The conical valve connector (4) is connected to filtration unit (5) by fitting over a superior aspect of the unit (5) to form the last part of the column (6).

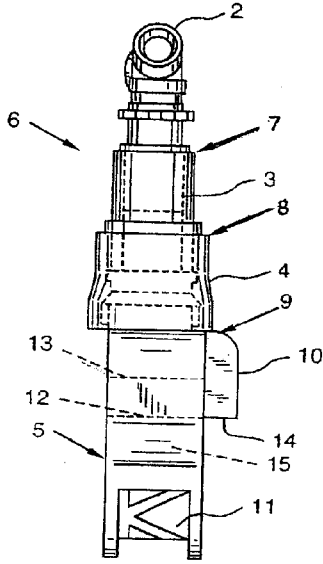

What is claimed is:

1. A tracheostomy breathing aid (1), comprised of:
a trach swivel adaptor (2) connected to a personal air filtration unit (5) comprised of an outer activated carbon pre-filter (11), an inner filter for particulate matter (12) and a one-way valve (13) in the form of a flap which allows air to be inhaled through said inner filter (12) but prevents exhaled air from entering a dead space (15) between filter (11) and filter (12), and an exhaust port (10) with one-way valve (14) in the form of a flap for allowing exhaled air to flow out of said unit (5), and preventing entering of inhaled air, thereby decreasing mixing of inhaled and exhaled air and resistance to exhalation, by a column (6) with a first end at said unit (5) and a second end at said adaptor (2) comprised of cylindrical multiadaptor valve connector (3) and conical valve connector (4), creating a distance between said adaptor (2) and unit (5), where from first end at said unit (5) to second end at said adaptor (2) is narrowing from first diameter at a wide inferior end of said conical connector (4) to second diameter at said adaptor (2).

2. A tracheostomy breathing aid (1) as in claim 1, in which the inner filter for particulate matter (12) filters material to as little as 0.1 microns in size.

3. The tracheostomy breathing aid (1) as in claim 1, in which the column (6) is formed by a first connection (7) of the trach swivel adaptor (2) to the cylindrical multiadaptor valve connector (3), in which the trach swivel adaptor (2) is inserted into the cylindrical multiadaptor valve connector (3), in turn connected to a second connection (8) of said cylindrical multiadaptor valve connector (3) to a narrow superior end of the conical valve connector (4), in which the cylindrical multiadaptor valve connector (3) is inserted into the narrow superior end of the conical valve connector (4), in turn connected to a third connection (9) of a wide inferior end of said conical valve connector (4) to said personal air filtration unit (5), in which the wide inferior end of said conical valve connector (4) fits over said personal air filtration unit (5), where said column (6) is wider at inferior end of said conical valve connector (4) than at narrow superior end of said conical valve connector (4), such that air from said unit (5) to said trach swivel adaptor (2) flows through said column (6) which is narrowing from first diameter at side wide inferior end of conical connector (4) where said connector (4) fits over said unit (5) to narrow end of conical connector (4) and then to cylindrical connector (3) which is inserted into narrow end of connector (4) and finally to said second diameter at trach swivel adaptor (2) inserted into connector (3).

4. A tracheostomy breathing aid (1) as in claim 3, in which said personal air filtration unit (5) serves through said one-way valve (13) in the form of a flap which prevents exhaled air from entering said dead space (15) and said exhaust port (10) with one way valve (14) in the form of a flap which allows exhaled air to flow out of said unit (5) thereby decreasing mixing of inhaled and exhaled air and resistance to exhalation, to counteract increased resistance to flow through said column (6) created by placement of connector (3) and connector (4) between said filter (5) and said adaptor (2) and by flow through a column (6) with a narrowing diameter from first end at said unit (5) with first diameter at wide inferior end of connector (4) to said second end at said adaptor (2) with second diameter at said adaptor (2).

5. A tracheostomy breathing aid (1) comprised of:

a trach swivel adaptor (2) connected to a personal air filtration unit (5) comprised of an outer activated carbon pre-filter (11), an inner filter for particulate matter (12) filtering material to as little as 0.1 microns in size and a one-way valve (13) in the form of a flap which allows air to be inhaled through said inner filter (12) but prevents exhaled air from entering a dead space (15) between filter (11) and filter (12), and an exhaust port (10) with one-way valve (14) in the form of a flap for allowing exhaled air to flow out of said unit (5), and preventing entering of inhaled air, thereby decreasing mixing of inhaled and exhaled air and resistance to exhalation, by a column (6) with a first end at said unit (5) and a second end at said adaptor (2) comprised of cylindrical multiadaptor valve connector (3) and conical valve connector (4) creating a distance between said adaptor (2) and unit (5), where from first end at said unit (5) to second end at said adaptor (2) is narrowing from first diameter at said wide inferior end of said conical connector (4) to second diameter at said adaptor (2), where said column (6) is formed by a first connector (7) of the trach swivel adaptor (2) to the cylindrical multiadaptor valve connector (3), in which the trach swivel adaptor (2) is inserted into the cylindrical multiadaptor valve connector (3), in turn connected to a second connection (8) of said cylindrical multiadaptor valve connector (3) to a narrow superior end of the conical valve connector (4), in which the cylindrical multiadaptor valve connector (3) is inserted into the narrow superior end of the conical valve connector (4), in turn connected to a third connection (9) of a wide inferior end of said conical valve connector (4) to said personal air filtration unit (5) in which the wide inferior end of said conical valve connector (4) fits over said personal air filtration unit (5), where said column (6) is wider at inferior end of said conical valve connector (4) than at narrow superior end of said conical valve connector (4), such that air from said unit (5) to said trach swivel adaptor (2) flows through said column (6) which is narrowing from first diameter at wide inferior end of conical connector (4) where said connector (4) fits over said unit (5) to narrow end of conical connector (4) and then to cylindrical connector (3) which is inserted into narrow end of connector (4) and finally to said second diameter at trach swivel adaptor (2) inserted into connector (3) and in which said personal air filtration unit (5), serves, through said one-way valve (13) in the form of a flap which prevents exhaled air from entering said dead space (15) and said exhaust port (10) with one way valve (14) in the form of a flap which allows exhaled air to flow out of said unit (5), thereby decreasing mixing of inhaled and exhaled air and resistance to exhalation, to counteract increased resistance to flow through said column (6) created by placement of connector (3) and connector (4) between said filter (5) and said adaptor (2) and by flow through a column (6) with a narrowing diameter from first end with first diameter at said wide inferior end of connector (4) to said second end with second diameter at said adaptor (2).

* * * * *

UNITED STATES PATENT AND TRADEMARK OFFICE
CERTIFICATE OF CORRECTION

PATENT NO. : 6,484,723 B2
DATED : November 26, 2002
INVENTOR(S) : Eileen Haas

It is certified that error appears in the above-identified patent and that said Letters Patent is hereby corrected as shown below:

Title page, Showing an illustrative figure, should be deleted and substitute therefor the attached title page.

Figure 4:
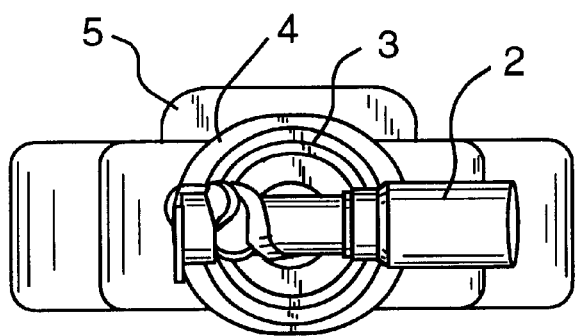
FIG. 4 is a top view of the invention
Figure 1:
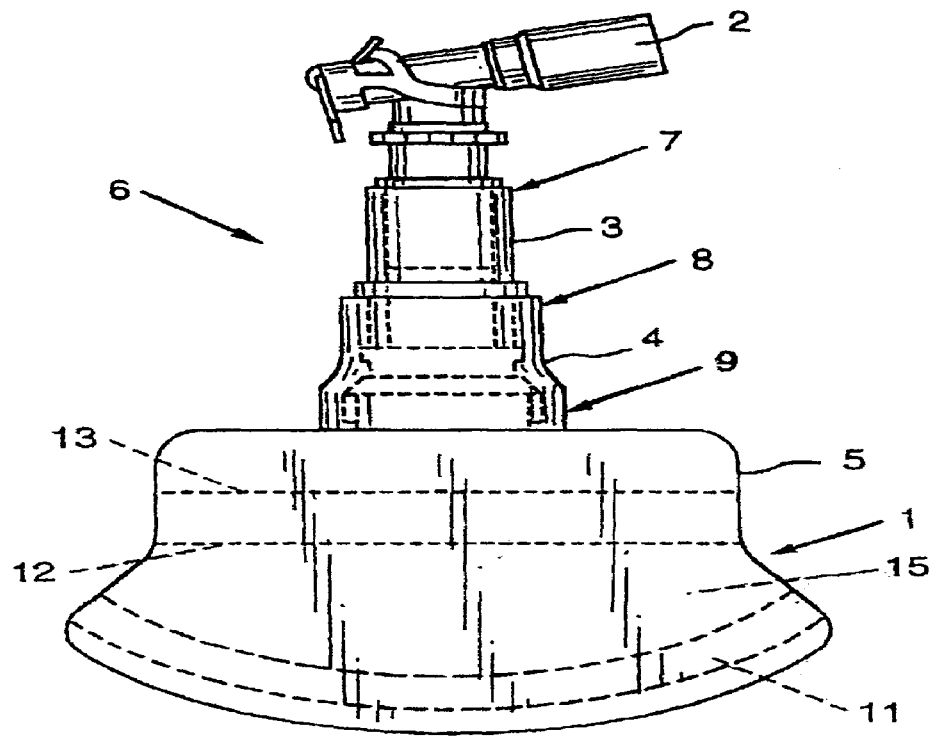
Figure 2:
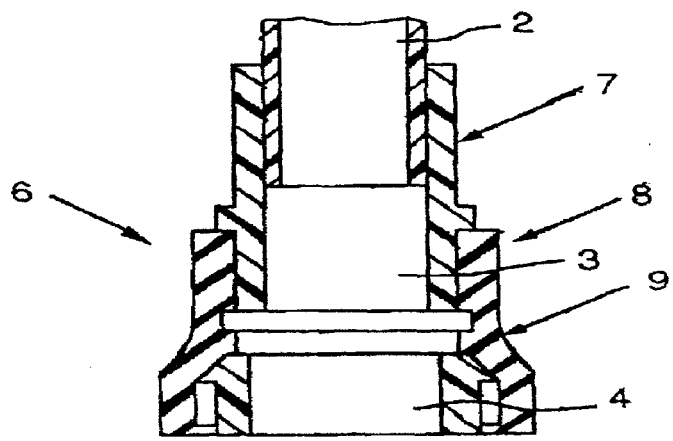
Figure 3:
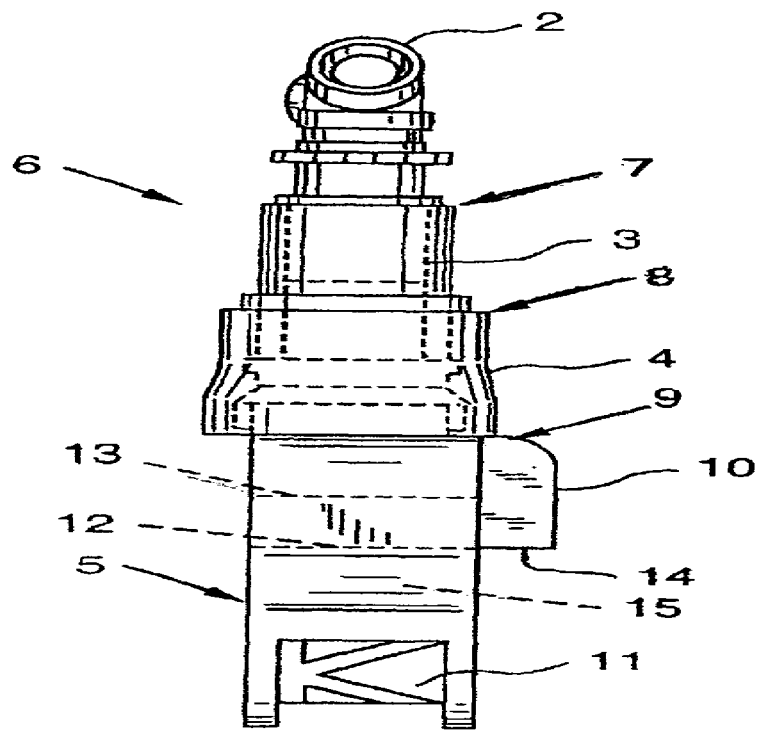
Figure 4:
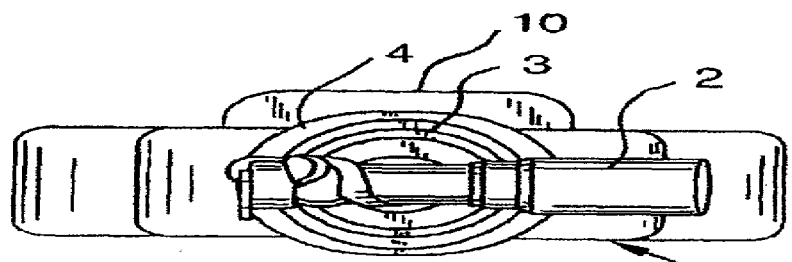

<u>Drawings,</u>
Delete Figures 1, 3 and 4, and substitute therefor the Figures 1, 3 and 4, as shown on the attached pages.

<u>Column 1,</u>
Line 24, "iner" should read -- inner --
Line 64, "proxhnally" should read -- proximally --

<u>Column 2,</u>
Line 2, "it's" should read -- its --
Line 4, "fixation" should read -- filtration --
Line 5, "preventing of" should read -- prevent --

<u>Column 4,</u>
Line 11, "resistence" should read -- resistance --

Signed and Sealed this

Sixth Day of May, 2003

JAMES E. ROGAN
*Director of the United States Patent and Trademark Office*

(12) United States Patent
Haas

(10) Patent No.: US 6,484,723 B2
(45) Date of Patent: Nov. 26, 2002

(54) TRACHEOSTOMY AIR FILTRATION SYSTEM

(76) Inventor: Eileen Haas, 90 Kaufman Rd., Gibsonia, PA (US) 15044

(*) Notice: Subject to any disclaimer, the term of this patent is extended or adjusted under 35 U.S.C. 154(b) by 0 days.

(21) Appl. No.: 09/249,682

(22) Filed: Feb. 11, 1999

(65) Prior Publication Data

US 2001/0013348 A1 Aug. 16, 2001

(51) Int. Cl.$^7$ .............................. A61M 16/00; A62B 9/06
(52) U.S. Cl. ........................ 128/207.14; 128/206.15; 128/207.16
(58) Field of Search ................. 128/200.26, 207.14, 128/207.15, 207.16, 205.27, 205.25, 205.24, 206.21, 206.15, 206.12

(56) References Cited

U.S. PATENT DOCUMENTS

| | | | | |
|---|---|---|---|---|
| 3,262,447 A | * | 7/1966 | Burke | 128/207.14 |
| 3,461,877 A | * | 8/1969 | Morch | 128/207.14 |
| 3,670,726 A | * | 6/1972 | Mahon et al. | 128/204.18 |
| 4,045,058 A | * | 8/1977 | Eross | 285/119 |
| 4,152,017 A | * | 5/1979 | Abramson | 285/260 |
| 4,416,273 A | * | 11/1983 | Grimes | 128/207.16 |
| 4,676,241 A | * | 6/1987 | Webb et al. | 128/207.14 |
| 5,022,394 A | * | 6/1991 | Chmielinski | 128/207.14 |
| 5,054,482 A | * | 10/1991 | Bales | 128/207.14 |
| 5,062,420 A | * | 11/1991 | Levine | 128/204.18 |
| 5,184,611 A | * | 2/1993 | Turnbull | 128/207.14 |
| 5,251,617 A | * | 10/1993 | Linder | 128/200.26 |
| 5,259,376 A | * | 11/1993 | Bales | 128/207.17 |
| D350,394 S | * | 9/1994 | Kazal | D24/164 |
| 5,368,734 A | * | 11/1994 | Wnenchak | 210/505 |
| 5,380,580 A | * | 1/1995 | Rodgers et al. | 428/219 |
| 5,496,507 A | * | 3/1996 | Angadjivand et al. | 264/423 |
| 5,666,950 A | * | 9/1997 | Smith | 128/207.14 |
| 5,694,922 A | * | 12/1997 | Palmer | 128/202.27 |
| 5,749,360 A | * | 5/1998 | Lacey et al. | 128/207.14 |
| 5,771,885 A | * | 6/1998 | Putrello | 128/205.27 |
| 5,840,091 A | * | 11/1998 | Strong | 55/385.1 |
| 5,890,488 A | * | 4/1999 | Burden | 128/200.26 |
| 6,119,691 A | * | 9/2000 | Angadjivand et al. | 128/206.19 |

* cited by examiner

Primary Examiner—Dennis Ruhl
Assistant Examiner—Joseph F. Weiss, Jr.
(74) Attorney, Agent, or Firm—Susan E. Nagel

(57) ABSTRACT

In the present invention, personal air filtration unit sold as SMARTMOUTH™, a trademark for a personal air filtration unit comprised of an outer activated carbon pre-filter and an inner filter for particulate matter available through Tri-Pact Enterprises has been attached to a column of valve connectors which are connected to a tracheostomy tube. The filter has a downwardly dependent exhaust port which allows expired air to flow out of the filtration unit without passing through the filters, thereby helping to prevent mixing of inhaled and exhaled air, and decreasing resistance to exhalation, as well as one-way valves in the form of a flap, on the one hand to prevent exhaled air from entering a dead space between filters, and on the other hand to prevent entering of inhaled air through the exhaust port.

5 Claims, 2 Drawing Sheets